United States Patent [19]
Whisenhunt et al.

[11] Patent Number: 4,748,281
[45] Date of Patent: May 31, 1988

[54] RECOVERY OF METHANOL IN AN MTBE PROCESS

[75] Inventors: David E. Whisenhunt; Gregg L. Byers; Uday S. Hattiangadi, all of Ponca City, Okla.

[73] Assignee: Conoco Inc., Ponca City, Okla.

[21] Appl. No.: 919,526

[22] Filed: Oct. 16, 1986

[51] Int. Cl.$^4$ ........................ C07C 41/06; C07C 41/36
[52] U.S. Cl. ..................................... 568/697; 568/699
[58] Field of Search ................................ 568/697, 699

[56] References Cited
U.S. PATENT DOCUMENTS
4,371,718  2/1983  Hutson .
4,409,421  10/1983  Schulwitz et al. .

FOREIGN PATENT DOCUMENTS
75136    3/1983  European Pat. Off. .
2448521  9/1980  France .

Primary Examiner—Howard T. Mars

[57] ABSTRACT

An adsorbent is used to recover methanol in unreacted $C_4$'s from the MTBE process. Methanol is desorbed from the mixture in a closed loop regeneration system utilizing a circulating vapor at an elevated temperature. Gas from the adsorber is cooled to condense methanol which may be recycled to the MTBE reaction. Unreacted $C_4$'s substantially free from methanol may be used in HF or sulfuric acid alkylation.

12 Claims, 1 Drawing Sheet

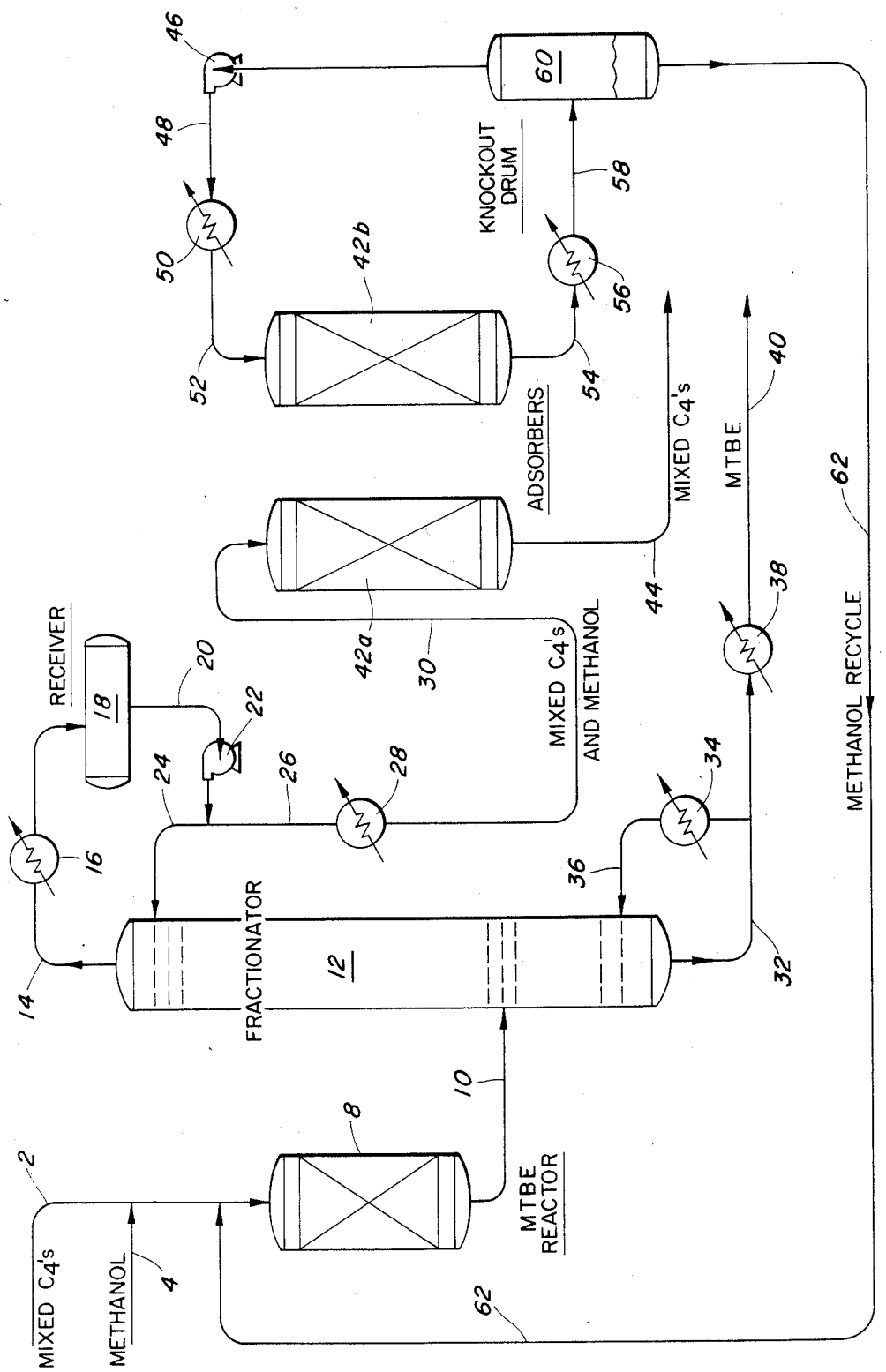

RECOVERY OF METHANOL IN AN MTBE PROCESS

BACKGROUND AND SUMMARY OF THE INVENTION

Methyltertiarybutylether (MTBE) is well recognized as a suitable blending stock for increasing the octane rating of gasoline. This material has been in use for sometime in Europe as a blending component with gasoline and the usage of MTBE in the United States is increasing. MTBE and related ethers, blended into gasoline at a 10 to 20 percent level, increase both motor and research octane numbers by several units.

MTBE is produced by reacting isobutylene with methanol. The reaction normally is conducted in the liquid phase and under relatively mild conditions. While mixed butylene streams can be used, only the tertiary olefin, isobutylene, reacts at the conditions employed. The catalyst normally used is an ion-exchange resin. The isobutylene component can be obtained from various sources such as naphtha cracking or catalytic cracking. Typically in a refinery a mixture of $C_4$'s (butanes-butenes) would be utilized as feedstock to the MTBE unit, with the unreacted $C_4$'s leaving the unit preferably being used as feed to an HF or sulfuric acid alkylation unit.

In HF alkylation it is known that too much water in the HF catalyst can adversely affect the alkylation reaction and can present problems of equipment corrosion. In addition, methanol is detrimental in the HF alkylation since methanol reacts with isobutane to produce unwanted, low octane, high volatility five carbon atom hydrocarbons and water, which undesirably dilutes the HF catalyst. Although to a lesser degree, materials such as methanol and MTBE also have a detrimental effect on the sulfuric acid alkylation. In view of this, methanol which remains in the $C_4$'s after fractionation for removal of the MTBE product must be removed prior to using the $C_4$'s in the alkylation step.

Conventional technology uses liquid-liquid extraction to remove methanol from the $C_4$ hydrocarbon stream (with water as the solvent), and fractionation of methanol from the water. Water is recycled to the extractor, and methanol is recycled to the MTBE reactors. Other schemes described in the art utilize an adsorbent to remove methanol from the $C_4$ hydrocarbon stream. Various $C_4$'s from within the MTBE unit are used to recover methanol by desorption for recycle to the MTBE reaction zone. When methanol contained in $C_4$'s is recycled to the MTBE reaction, control of fresh methanol to the process must be corrected to allow for varying rates of recycle methanol recovered from the adsorbers. The process is then unsteady state. If the fresh methanol rate is not adequately reduced to account for recycle methanol, loading to the adsorption system is increased, potentially to the extent that capacity of the system becomes inadequate. If the fresh methanol feed rate is overcompensated for recycle, isobutene conversion, and hence MTBE production, is unnecessarily reduced. The unsteady state problem can be solved by introducing surge capacity into the system but the large surge capacity requirements increase the capital cost of the process.

In the method of this invention, an adsorbent is used to recover methanol and unreacted $C_4$'s from the MTBE process. Methanol is desorbed in a closed loop regeneration system in which a circulating vapor is passed through the adsorbent at an elevated temperature. Desorbed methanol exits with the circulating vapor which is cooled to condense the methanol. Liquid methanol is removed from the system and recycled to the MTBE reaction. The purified $C_4$ stream provides an excellent feedstock for the HF alkylation reaction.

The method of this invention recovers methanol in sufficiently high purity that only minimal liquid surge capacity is needed to allow the methanol to be recycled at a constant flow rate to the MTBE reaction. This eliminates unsteady state control problems and allows a minimum size of adsorption system for the maximum production of MTBE. The unreacted $C_4$'s stream recovered from the adsorption step is water-free so that it does not need to be dried prior to entering the alkylation unit. In contrast if conventional water wash is used to remove methanol, the $C_4$ stream is saturated with water and requires dehydration prior to alkylation.

PRIOR ART

U.S. Pat. Nos. 4,371,718, 4,409,421 and European Patent Application No. 75136 all disclose adsorption-desorption systems for removing methanol from a mixture of $C_4$'s. In each of these references the methanol-loaded adsorbent is desorbed with a process feed or product stream.

BRIEF DESCRIPTION OF THE DRAWING

The drawing is a schematic flow diagram of an MTBE unit which illustrates the invention.

DETAILED DESCRIPTION OF THE INVENTION

Referring now to the drawing, mixed $C_4$'s (butanes and butenes) and methanol are introduced through lines 2 and 4, respectively, to MTBE reactor 8 wherein the methanol reacts with isobutylene in the mixed $C_4$'s to form MTBE. The conversion of isobutylene and methanol to MTBE can be carried out under any suitable reaction conditions. The mole ratio of methanol to isobutylene usually is in the range of about 0.05 to about 10, more usually about 0.1 to 5 and preferably about 1 to 1. The reaction temperature may vary from about 60° F. to about 300° F. but more usually the reaction is carried out at a temperature of from about 120° F. to about 200° F. The pressure employed is sufficient to maintain the reactants in the liquid phase and is typically in the range of about 30 psig to about 300 psig.

The reaction usually employs an acid-type ion-exchange resin such as a high molecular weight carbonaceous material containing sulfonate groups. Sulfonated resins of various types are widely available under various commercial names and of various types such as the sulfonated coals, phenol formaldehyde resins reactive with sulfuric acid, sulfonated resinous polymers of cumerone-indene with cyclopentadiene, various commercially available strongly acidic cationic exchange resins such as sulfonated polystyrene resins and various others. The catalyst is employed in a finely divided state in a mesh size of about 10 to 50 US sieve. Preferably a fixed bed of particulate solid ion-exchange resin catalyst, e.g. such as Amberlyst 15 is used to carry out the reaction.

Effluent from reactor 8 comprising isobutane, normal butane, straight chain butylenes, a small amount of unreacted isobutylene, a small amount of unreacted methanol, and product MTBE is introduced through line 10 to fractionator 12. Product MTBE is removed from the bottom of the fractionator via conduit 32, passed through cooler 38, and then through line 40 to storage. The heat required for reboiling the tower is provided by passing a portion of the MTBE through heater 34 and returning it to the bottom of the tower through line 36. Methanol forms an azeotrope with butenes contained in the MTBE reactor effluent therefore it is not possible to separate this material by fractionation. As a result the overhead from the fractionator contains a mixture of $C_4$'s and unreacted methanol. This mixture leaves the fractionator via line 14 and condenser 16 and accumulates in receiver 18. A portion of the condensed overhead is returned to the fractionator as reflux through line 20, pump 22, and line 24. The remainder of the overhead passes via line 26 through cooler 28 (if cooling is required) and is introduced through line 30 into the top of adsorber 42a wherein methanol is adsorbed from the mixed $C_4$'s. Adsorption may be carried out with any absorbent suitable for the retention of methanol such as alumina, silica gel, molecular sieve, ion-exchange resin, or other materials well known in the art. Adsorption is carried out under conditions which are suitable to effect removal of methanol from the $C_4$'s and include temperatures of between about 50° F. and about 200° F., pressures between about 50 psig and about 300 psig. Feed flow rate is controlled to provide a WHSV of between about 0.5 and about 15. The time required for adsorption will depend on the amount and type of adsorbent used and the operating conditions employed, but will usually be between about 2 and about 12 hours.

During the adsorption process mixed $C_4$'s substantially free of methanol are removed from the bottom of the adsorber through line 44. If desired, these $C_4$'s can be utilized as an excellent feed material to the alkylation process. When the adsorbent in 42a becomes spent (saturated with methanol) the feed stream is switched to another adsorber (not shown). The spent adsorbent is then regenerated to recover the methanol and place the adsorbent in condition for re-use. In the drawing the regeneration operation is shown in adsorber 42b. Regeneration is carried out in a closed circuit with a circulating gas provided from blower 46. This gas passes via line 48 into heater 50 where it is heated to a sufficient temperature to effect desorption of methanol. The heated gas is introduced to desorber 42b through conduit 52 wherein it releases and picks up methanol from the adsorbent. The mixture of circulating gas and methanol exiting the adsorber through line 54 is cooled in cooler 56 to condense the methanol which is then introduced with the circulating gas via line 58 into knockout drum 60. Methanol accumulates in the bottom of the knockout drum and from there is recycled through line 62 to MTBE reactor 8. The circulating gas is pulled from the knockout drum by blower 46 and recycled to adsorber 42b. This operation is continued until the adsorbent is substantially freed of methanol at which time the adsorber is returned to adsorbent service. Operating conditions employed in carrying out the desorption (regeneration) process include temperatures in the range of about 200° F. to about 500° F., pressures between about 50 psig and about 300 psig and a WHSV from about 0.5 to about 3. The time required for desorption will usually be in about the same range as for adsorption, namely between about 2 and about 12 hours.

The circulating gas stream used in the desorption step may be any gas which remains vapor at the system operating temperature and pressure and does not react with methanol or the adsorbent at the operating conditions employed and does not foul the adsorbent. Gases which may be used include nitrogen, carbon dioxide, hydrocarbon gases, such as methane, ethane and propane and other inert gases.

The following examples illustrate the results obtained in carrying out the invention.

EXAMPLES

Silica gel was used as the adsorbent in 56 adsorption/desorption cycles with a feed of mixed $C_4$'s containing methanol and utilizing closed loop nitrogen gas regeneration. Cycle lengths were about 2–3 hours for both adsorption and desorption. Adsorption (loading) and desorption were considered complete at a level of 100 ppm of methanol in the adsorber effluent. The following table summarizes the operating conditions employed.

TABLE

| Cycles* | Desorption Conditions |
| --- | --- |
| 1–22 | 300° F., 90 psig, 5 WHSV, Nitrogen Only |
| 23–44 | 300° F., 90 psig, 5 WHSV, 2.1% MeOH in $N_2$ |
| 45–50 | 400° F., 90 psig, 5 WHSV, 2.1% MeOH in $N_2$ |
| 51–56 | 400° F., 90 psig, 5 WHSV, Nitrogen Only |

*All adsorptions were carried out at 100° F., 120 psig, 5 WHSV, with 0.5% MeOH in $C_4$'s.

In each cycle the mixed $C_4$'s leaving the adsorber were monitored with a chromatograph and contained less than 10 ppm methanol. Methanol loading of the silica gel was about 10.0 weight percent for the cycles at 300° F. with nitrogen only as the desorbant gas. For the other cycles (23 through 56) the methanol loading varied from 6.0 to 6.3 weight percent.

We claim the following:

1. In a process for the manufacture of methyltertiarybutylether (MTBE) in which methanol and a mixture of $C_4$ hydrocarbons containing isobutylene are contacted in a reaction zone containing an ion-exchange resin catalyst under suitable conditions to effect the reaction of methanol and isobutylene to produce a reaction product containing MTBE, unreacted methanol, unreacted isobutylene and other $C_4$ hydrocarbons; the reaction product is introduced to a fractionation zone wherein it is separated into a bottoms product comprising essentially MTBE and an overhead product containing unreacted methanol, unreacted isobutylene and other $C_4$ hydrocarbons; and the overhead product is introduced to an adsorption zone wherein the methanol is adsorbed; the improvement which comprises utilizing silica gel as adsorbent and regenerating the silica gel adsorbent in a closed loop by contacting the silica gel adsorbent with a desorption gas stream at an elevated temperature for a sufficient period of time to remove adsorbed methanol, cooling the effluent from the adsorption zone to condense desorbed methanol, removing desorbed methanol from the system and recycling the desorption gas to the adsorption zone.

2. The process of claim 1 in which the heat for the desorption of methanol from the adsorbent is provided by heating the desorption gas prior to its introduction to the adsorption zone.

3. The process of claim 2 in which the desorption gas is selected from the group consisting of nitrogen, carbon dioxide, methane, ethane and propane.

4. The process of claim 3 in which desorbed methanol is recycled to the reaction zone.

5. The process of claim 4 in which unreacted isobutylene and other C₄ hydrocarbons leaving the adsorption zone are utilized as feed to an alkylation unit.

6. The process of claim 5 in which regenerated adsorbent is reused for the adsorption of methanol.

7. In a process for the manufacture of methyltertiarybutylether (MTBE) in which methanol and a mixture of C₄ hydrocarbons containing isobutylene are contacted in a reaction zone containing an ion-exchange resin catalyst under suitable conditions to effect the reaction of methanol and isobutylene to produce a reaction product containing MTBE, unreacted methanol, unreacted isobutylene and other C₄ hydrocarbons; the reaction product is introduced to a fractionation zone wherein it is separated into a bottoms product comprising essentially MTBE and an overhead product containing unreacted methanol, unreacted isobutylene and other C₄ hydrocarbons; the improvement comprising passing the overhead product to a silica gel adsorption zone wherein methanol is adsorbed by said silica gel, at a temperature between about 50° F. and about 200° F., a pressure between about 50 pounds per square inch gauge (psig) and about 300 psig and a feed rate weight hourly space velocity (WHSV) between about 0.5 and about 15; regenerating the silica gel adsorbent in a closed loop by contacting the silica gel adsorbent with a desorption gas stream at a temperature between about 200° F. and about 500° F., a pressure between about 50 psig and about 300 psig and a WHSV from about 0.5 to about 3 for a sufficient period of time to remove adsorbed methanol, cooling the effluent from the adsorption zone to condense desorbed methanol, removing desorbed methanol from the system and recycling desorption gas to the adsorption zone.

8. The process of claim 7 in which the heat for the desorption of methanol from the adsorbent is provided by heating the desorption gas prior to its introduction to the adsorption zone.

9. The process of claim 8 in which the desorption gas is selected from the group consisting of nitrogen, carbon dioxide, methane, ethane and propane.

10. The process of claim 9 in which desorbed methanol is recycled to the reaction zone.

11. The process of claim 10 in which unreacted isobutylene and other C₄ hydrocarbons leaving the adsorption zone are utilized as feed to an alkylation unit.

12. The process of claim 11 in which regenerated adsorbent is reused for the adsorption of methanol.

* * * * *